United States Patent [19]

Hurley

[11] Patent Number: 5,061,076
[45] Date of Patent: Oct. 29, 1991

[54] TIME-RESOLVED FLUOROMETER

[75] Inventor: Ian Hurley, Staten Island, N.Y.

[73] Assignee: Enzo Diagnostics, Inc., Farmingdale, N.Y.

[21] Appl. No.: 304,748

[22] Filed: Jan. 31, 1989

[51] Int. Cl.⁵ .................. G01N 21/25; G01N 33/544; F21V 9/16

[52] U.S. Cl. .............................. 356/417; 250/458.1; 436/528; 436/529; 436/517; 436/805; 436/172; 356/318

[58] Field of Search .................. 250/238, 458.1, 459.1, 250/461.1, 461.2; 350/1.6; 356/317, 318, 410, 417; 436/528, 529, 172, 517, 805; 422/65, 55

[56] References Cited

U.S. PATENT DOCUMENTS

| | | | |
|---|---|---|---|
| 3,327,126 | 6/1967 | Shannon et al. | 250/238 |
| 3,829,696 | 8/1979 | Birnbaum | 250/461.1 |
| 4,058,732 | 11/1977 | Wieder | 436/529 |
| 4,311,387 | 1/1982 | DeMey et al. | 356/410 |
| 4,419,583 | 12/1983 | Noeller | 250/461.2 |
| 4,663,557 | 5/1987 | Martin, Jr. et al. | 350/1.6 |
| 4,724,217 | 2/1988 | Miller | 250/458.1 |
| 4,786,170 | 11/1987 | Groebler | 250/458.1 |
| 4,791,310 | 12/1988 | Honig et al. | 250/461.2 |
| 4,802,768 | 2/1989 | Gifford et al. | 356/417 |
| 4,868,103 | 2/1989 | Stavrianopoulos et al. | 435/803 |
| 4,927,265 | 5/1990 | Brownlee | 356/73 |
| 4,940,332 | 7/1990 | Miwa et al. | 356/417 |

OTHER PUBLICATIONS

"Laser Induced Fluorometric Analysis of Drugs," Strojny et al., Anal. Chem. No. 11, Sep. 1980, pp. 1554-1559.
"Scanned-laser Microscope for Photoluminescence Studies", Black et al., Applied Optics, vol. 11, No. 7, Jul. 1972, pp. 1553-1562.
Syvanen et al., Nucleic Acids Research 14:1017-1028.
Soini et al., Clin. Chem. 29:65-68 (1983).

Primary Examiner—F. L. Evans
Assistant Examiner—K. P. Hantis
Attorney, Agent, or Firm—Elaine P. Brenner; Ronald C. Fedus

[57] ABSTRACT

A time-resolved fluorometer, having a light tight enclosure, for detecting the presence of an analyte in a sample. Within the light tight enclosure are a pulsed dye laser that produces a pulsed light beam for sample excitation, a light tight sample excitation station through which samples, treated with a reagent composition, are passed into the path of the pulsed light excitation beam to produce a delayed fluorescence emission, a fused silica lens system through which the delayed fluorescence emission passes and an assembly which selectively amplifies, counts and characterizes the resulting emissions. The operation and coordination of the time resolved fluorometer are under computerized control as are the readings reported. Significant improvements relate to the fused silica lens systems and interference filters, cooling of the emission measurement apparatus and particularly the improved performance resulting from the combination of these aspects.

27 Claims, 2 Drawing Sheets

TIME-RESOLVED FLUOROMETER

BACKGROUND OF THE INVENTION

1. Field of the Invention

This invention relates to improvements in time-resolved fluorometers, particularly those useful for determining delayed fluorescence emission in clinical and other samples. More particularly, it relates to time-resolved fluorometers having diminshed instrument-produced background fluorescence.

2. Brief Description of the Prior Art

Fluorescent compounds are frequently used as labeling compounds in a broad range of assay systems, particularly those used for determining analytes of clinical interest. It has been recognized that many types of biological specimens in which such analytes are to be detected naturally fluoresce, thereby creating a natural background fluorescence which limits the sensitivity of the assay systems used to detect such analytes.

One approach to avoiding this problem has been the use of fluorescent labels, such as lanthanide chelates, which produce a time-delayed or time-resolved fluorescence which is measurable after the decay of the natural fluorescence of the biological sample. See, for example, Syvanen, et al.,*Time-resolved fluorometry: a sensitive method to quantify DNA-hybrids*, Nuc. Ac. Res., 14:1017–1028(1986).

Instruments have been developed to measure the time-resolved fluorescence produced by these assay systems. For example, Soini, et al., *Time-Resolved Fluorometer for Lanthanide Chelates-A New Generation of Nonisotopic Immunoassays*, Clin. Chem., 29:65–68(1983) discloses a manually operated fluorometer for assays using lanthanide chelates as labels.

Another such instrument is disclosed by Wieder, U.S. Pat. No. 4,058,732. The fluorometer disclosed here, like the one described by Soini, uses a laser light source to excite a reagent in a fluorescent assay composition and reads the time-delayed fluorescent signal with a photomultiplier tube.

Notwithstanding the avoidance of autofluorescence in biological samples achieved by time-delayed or time-resolved fluorescence, recognition of the limitations of instruments in this field in their own production of background fluorescence has not been documented, addressed or overcome.

SUMMARY OF THE INVENTION

In contrast, the present invention has resulted from a recognition of and solution to the problem of fluorescence resulting from instruments so far used to measure time-delayed or time-resolved. The full sensitivity of presently available time-delayed fluorescence reagent compositions can now be realized with the limitations of associated instrumentation having been overcome.

The invention provides a time-resolved fluorometer for detecting the presence of an analyte in a sample, which fluoromete comprises a light tight enclosure having therein:

means for emitting a beam of excitation light;

a light tight sample excitation station for a sample which has been reacted with a reagent composition excitable by said excitation light to produce a delayed fluorescence in the presence of said analyte, which excitation station comprises a light tight sample enclosure provided with an excitation beam inlet and a delayed fluorescence outlet;

a fused silica lens system for delivering said excitation beam to said sample in said sample enclosure;

sample handling means capable of positioning the so-reacted sample in the path of said excitation beam within said sample enclosure;

means for measuring delayed fluorescence emitted from the so-reacted sample; and a fused silica lens system for delivering the delayed fluorescence emitted from the sample to said delayed fluorescence measuring means.

In a further aspect of the invention, the means for measurement of delayed fluorescence is a thermoelectrically cooled photomultiplier.

Using the sensitivity calculation method adopted in the literature cited above, the invention makes it possible in preferred embodiments to count 1,300 times more photons per pulse than has previously been possible. An additional reduction in background counts by a factor of 100 is made possible by cooling the photomultiplier.

DESCRIPTION OF THE PREFERRED EMBODIMENTS

Although specific terms are used in the following description for clarity, they refer only to the particular embodiment(s) selected for illustration and are not a limitation of the scope of the invention.

Figure 1:
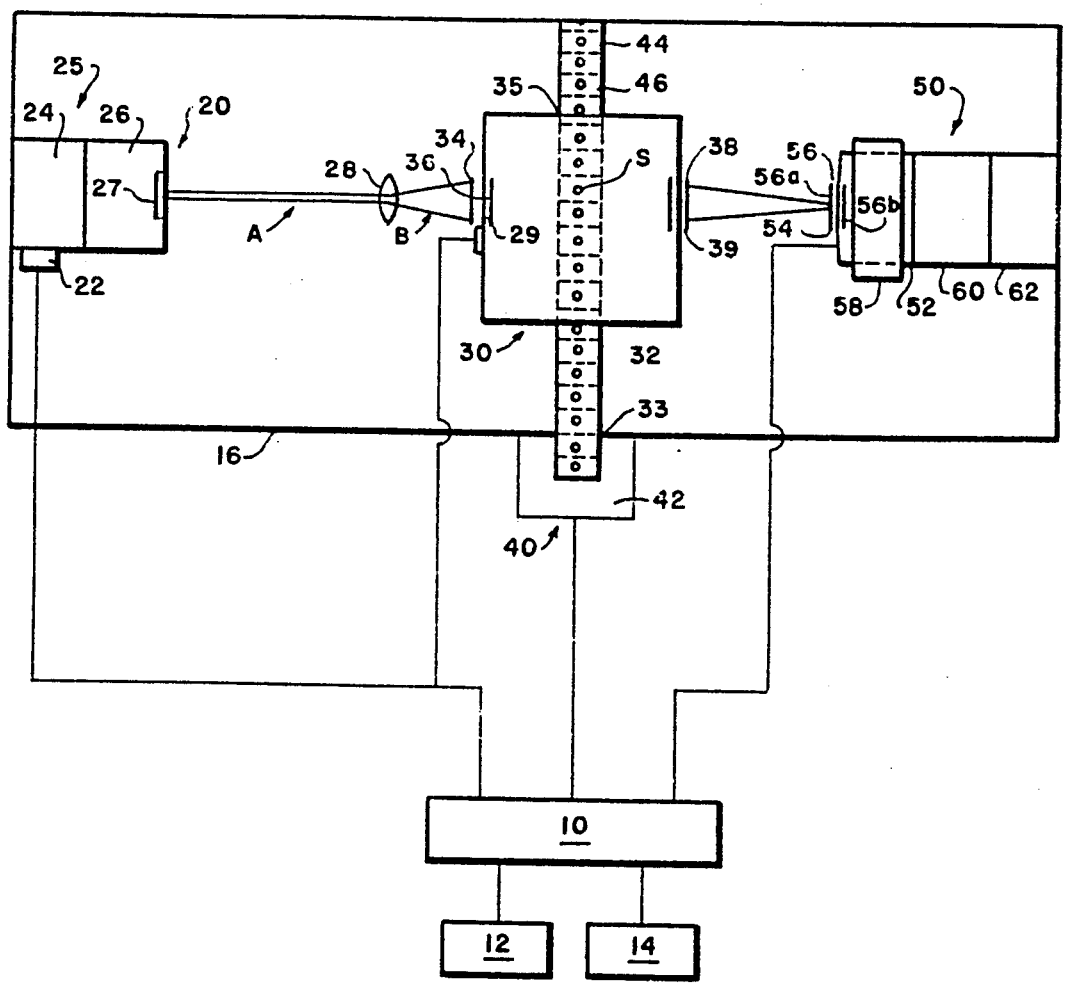
FIG. 1 is a schematic diagram of one preferred embodiment of the time-resolved fluorometer of the invention.

Referring now to FIG. 1, controller 10 is a general purpose digital computer with a stored (fixed) program which is connected with user console 12 and recorder 14. User console 12 conventionally includes a printer for recording the test data of each analysis. Controller 10 instructs, monitors and controls the sequence and coordination of system operations, as more fully described below, as well as calculates and monitors the quality of results and provides data output in a variety of formats.

Light tight enclosure or housing 16 contains, inter alia, laser assembly 20 which includes trigger 22, pulsed dye laser unit 25, laser beam spreader 28 and laser output monitor 29. Pulsed dye laser unit 25 is activated by laser trigger 22, as controlled by controller 10, and includes nitrogen laser 24, dye laser 26 and interferometer 27. Nitrogen laser 24 consists essentially of a sealed nitrogen plasma cartridge and associated excitation electronics (not shown) that produce a 5 nanosecond(ns) pulse of light at 337 nanometers(nm) upon activation by an external trigger signal from laser trigger 22. Dye laser 26 is excited by the pulse so-produced to emit a laser light pulse at about 405 nm. This lasing is produced in dye laser 26 when an excitation pulse strikes a saturated solution of p-diphenylstilbene in dioxane, which is strongly fluorescent when excited. The 405 nm wavelength is selected by interferometer 27, a component of dye laser 26 that permits passage of light having multiples of the 405 nm wavelength. A suitable embodiment of laser unit 24 is the LSL Dye Laser (Laser Science, Inc., Cambridge, MA). The 405 nm laser light pulses produced by dye laser 26 are referred to as laser beam A, a 0.8 millimeter (mm) wide laser beam that passes into beam spreader 28. Beam spreader 28 comprises a microscope objective lens having a 4 mm focal length (not shown) and a collimating lens (not shown). A suitable objective lens is the Nikon MSK 10401 40X objective lens. A suitable collimating lens is an Ealing 34-6734 plano-convex lens (Ealing Optical, Needham, MA) having a 38.3 mm focal length and 25.4 mm diameter. Beam spreader 28 produces sample excitation beam B which is monitored by laser output monitor 29 under the control of controller 10.

Sample excitation assembly 30 includes light tight housing 32 having sample inlet 33, excitation beam inlet 34, sample outlet 35 and delayed fluorescence outlet 38. Excitation beam inlet 34 and delayed fluorescence outlet 38 are provided with interference filter 36 and convergent lens 39, respectively. A particularly preferred embodiment of sample excitation assembly 30 is shown in more detail in FIG. 2, as described below.

As a component of the fused silica lens system for delivery of sample excitation light of the invention, interference filter 36 is of metal on a fused silica base, passes 405 nm sample incident beam B and reflects sample emission of 565 nm or more. A suitable interference filter is a 1.0 cm diameter 405 nm interference filter (Omega Optical, Inc., Brattleboro, VT).

As a component of the fused silica lens system for delivering delayed fluorescence emission from the sample for measurement, convergent lens 39 is an Ealing 34-6809 fused silica plano-convex lens (Ealing Optical, supra) having a 100 mm focal length and 50.8 mm diameter.

As a further component of the fused silica lens system for delivering sample emission for measurement, interference filter 56 is comprised of an outer edge filter 56a and an inner narrow pass interference filter 56b. Outer edge filter 56a is constructed on a fused silica substrate, permits a band pass of 565–750 nm wavelength, and is 50.8×50.8 mm in size (Omega Optical Co., Brattleboro, VT). Outer filter 56a is so-constructed to prevent scattered incident radiation or direct fluorescence from reaching inner filter 56b, thereby causing it to autofluoresce. Inner filter 56b is deposited on a conventional glass substrate and is also 50.8×50.8 mm in size. Inner filter 56b permits selection of an advantageous wavelength for observing delayed fluorescence. For example, a 620 nm band-pass filter (Ealing #35-3870) is preferred for delayed fluorescence emanating from europium.

Sample handling assembly 40 includes sample delivery station 42 and endless loop 44 comprising a sequence of sample holder units 46. The sample handling assembly can be any of a number of conventional formats (not shown), such as those in which the endless belt is formed of sample holder units designed to position for excitation a sample-containing analytical element or vessel. Such analytical element or vessels can include test strips, slides, capillary tubes or the like, preferably formed of fused silica rather than conventional materials, to reduce or eliminate system background fluorescence in accordance with the invention. Alternatively, the sample handling assembly can be at least a portion of the fluid handling conduits (not shown) of a continuous flow analyzer, such as that described in Smith, et al., EPO Patent Publication No. 0 200 235. In any of these embodiments, sample handling, positioning within sample excitation assembly 30 and coordination with the operation of other components of the instrument is under control of controller 10.

Detector assembly 50 includes photomultiplier tube 52, amplifier/discriminator 60 and pulse counter 62. Pulse counter 62 is connected and delivers data to controller 10 through a parallel interface board (not shown). Photomultiplier tube 52 includes photomultiplier tube inlet 54 provided with interference filter 56 and thermoelectric solid state cooler 58.

In accordance with the invention, photomultipliers having high sensitivity in the red range and a broad dynamic range are used. These can count an exceptionally high number of counts per second (up to 10–12 million) as compared with those conventionally used. An appropriate photomultiplier tube 52 is the Hammamatsu PMT(R943-02), having a gallium arsenide photocathode (Hammamatsu Corporation, Bridgewater, NJ). Photomultiplier tube 52 is powered by a conventional D.C. power supply (not shown).

Further in accordance with the invention, photomultiplier tube 52 is cooled to a constant temperature of about −40° C. during operation. Temperature is monitored by a copper-constantan thermocouple in contact with the inner wall of the phototube container and maintained constant under the control of controller 10. This reduces spurious counts from thermal electrons inside photomultiplier tube 52 to about 1–3 Hz as compared to 100 Hz reported by others in the literature, thereby increasing sensitivity potential by a factor of about 100.

Figure 2:
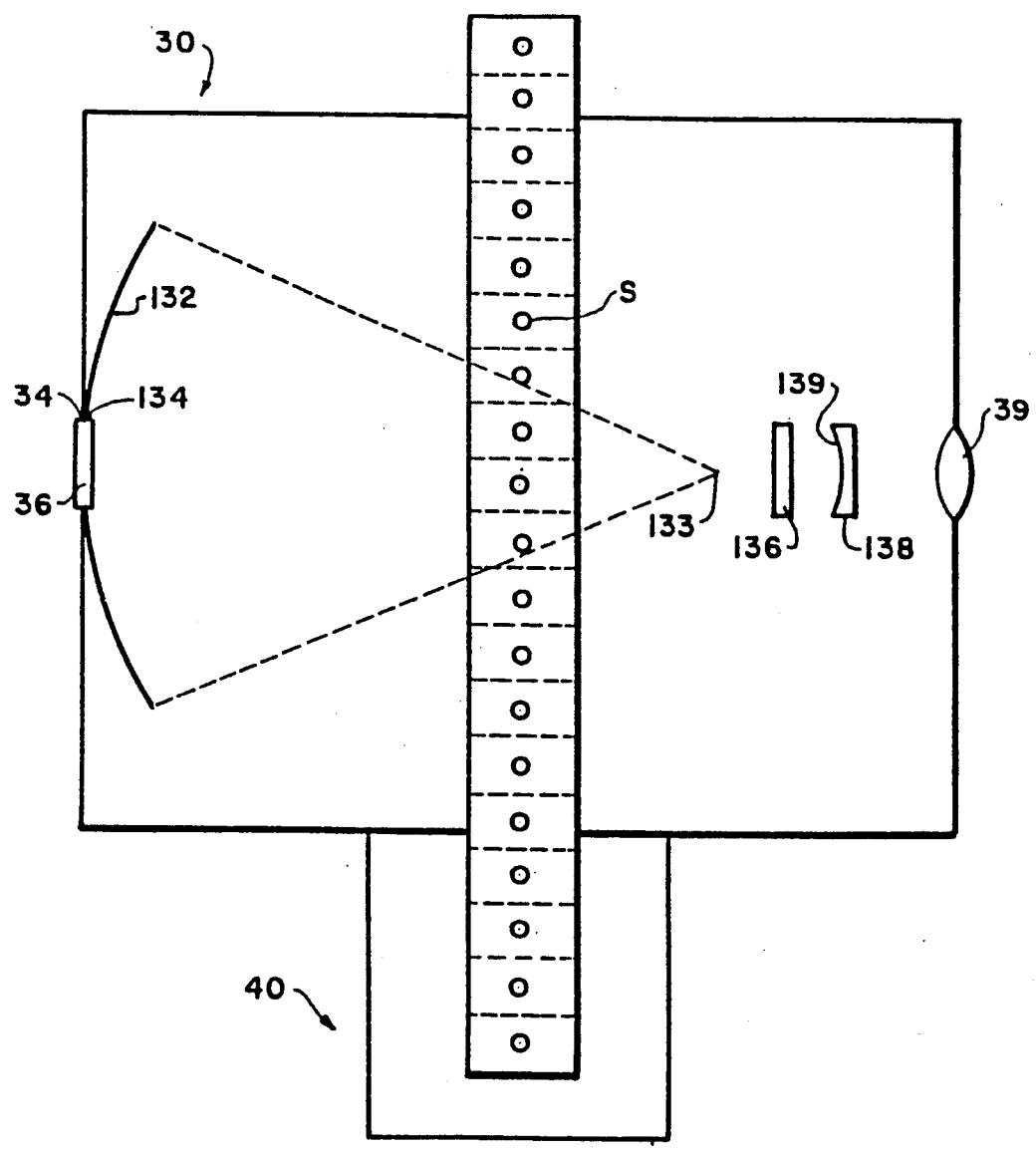
FIG. 2 is an enlarged view of a preferred embodiment of the sample excitation assembly and components of the fussed silica lens systems.

Referring now to FIG. 2, sample excitation assembly 30 includes an Edmund #E42,842 front surface parabolic mirror 132 (Edmund Scientific, Barrington, NJ) having a 50 mm diameter, −23 mm focal length and, also, aperture 134 at the center thereof. Parabolic mirror 132 is positioned in excitation assembly 30 such that aperture 134 is adjacent to and coextensive with excitation beam inlet 34. In this way, parabolic mirror 132 does not interfere with the light entering through interference filter 36. Focal point 133 of parabolic mirror 132 is along the path of sample excitation beam B and between the position where the sample S is held for reading and secondary interference filter 136, as further discussed next below.

Still referring to FIG. 2, excitation assembly 30 also includes a secondary 405 nm band pass interference filter 136, which is identical to interference filter 36 (described above), and a 1.0 cm diameter, 0.3 cm thick aluminum beam-stopper disc 138 which are positioned between interference filter 36 and convergent lens 39 along the path of the sample incident beam. Aluminum beam-stoper disc 138 has a concave surface 139 facing the source of the sample incident beam.

The time-delayed fluorometer of the invention is particularly suitable for use in conjunction with specific binding assys, such as immunoassays and nucleic acid hybridization assays, on body fluid, tissue section or other physiological samples. Such samples can include biological fluids, such as whole blood, serum, plasma, urine, cerebrospinal fluid, saliva, milk, culture media and supernatants as well as fractions of any of them. Tissue sections can be, for example, fresh, frozen or paraffin embedded. Other sources of sample fluid which are tested by conventional methods are contemplated and can also be assayed in accordance with the invention.

The analyte can be any substance, or class of related substances, whose presence in the sample is to be qualitatively or quantitatively determined. The fluorometer of the invention can operate in conjunction with assay compositions for the detection of analytes for which there is a specific binding partner and, conversely, for the detection of the capacity of a sample to bind an analyte (usually due to the presence in the sample of a binding partner for the analyte). The analyte usually is an oligo- or polynucleotide, oligo- or polypeptide, oligo- or polysaccharide, steroid or other organic molecule for which a binding partner exists or can be provided by immunological or synthetic means. Functionally, the analyte is usually selected from an RNA or DNA for which a complementary nucleic acid sequence exists or can be made, antigens or haptens and antibodies thereto, and hormones, vitamins, metabolites and pharmacological agents and their receptors and binding substances.

The specific binding partner for the analyte can be any compound or composite capable of recognizing a particular spatial and polar organization of a molecule, such as an epitopic site, or a particular informational sequence, such as a nucleic acid sequence, in preference to other substances. In the majority of embodiments, the specific binding partner will be a specific binding assay reagent, such as a nucleic acid hybridization assay probe, a mono- or polyclonal antibody, other specific binding protein or saccharide-specific lectin.

COMPARATIVE BACKGROUND FLUORESCENCE REDUCTION

In accordance with the invention, it has now been recognized that ordinary glass lenses and interference filters are unsuitable for this purpose because of their unacceptable high autofluorescence.

During the considerable efforts that have gone into research on and development of preferred embodiments of the instrument disclosed in accordance with the invention, it was found that replacing optical components of the instrument which had been made of conventional materials, such as those taught for use by the prior art in this field, with fused silica optical components greatly improved the performance of such instruments by reducing the number of background or non-specific counts of fluorescence.

When the filter identified as element 56a was replaced by a 50.8×50.8 mm, 570 mm long pass filter (Schott OG-570), 2410 counts/second were recorded from a 0.45 micron filtered distilled water sample in a 1.0 cm path length fused silica cell which was placed in the optical train at a point equivalent to the position of sample holder 40 in an otherwise identical instrument. Under the same conditions of measurement, the instrument having the filter formed on a fused silica substrate 56a typically gave 3–40 counts/second.

In another comparison, interference filter 36 was removed and replaced with a conventional 405 nm interference filter (Ealing #35-8069). With the conventional filter in place, a 30-times-higher counting rate (76,100 counts/second) was measured than when no filter was present at this position.

When fused silica convergent lens 39 was replaced with an otherwise-equivalent crown glass lens (Ealing #30-8858), 23,500 counts were produced from filtered distilled water.

The excess counts reported above decayed after the end of the laser pulse, following first order kinetics, within a characteristic time of 470 microseconds. This is too long for the fluorescence to be ascribed to a dissolved species in the water samples at room temperature. These counts are therefore attributed to autofluorescence associated with trace metal ion impurities present in conventional glass used in conventional lens systems and which is absent in fused silica.

The results of these comparative experiments, performed with different lens system components on the exact same instrument, dramatically demonstrate the improvement in performance of the instrument system and thus its availability to take full advantage of the sensitivity of the best fluorescent assay reagent technologies available now and in the future.

Although the invention has been described with particularity, numerous changes in the details, combinations and arrangement of elements can be made without departing from the scope of the invention as conceived, described and claimed.

What is claimed is:

1. A time-resolved fluorometer for detecting the presence of an analyte in a sample, which fluorometer comprises a light tight enclosure having therein:
    means for emitting a beam of excitation light;
    a light tight sample excitation station for a sample which has been reacted with a reagent composition excitable by said excitation light to produce a delayed fluorescence in the presence of said analyte, which excitation station comprises a light tight sample enclosure provided with an excitation beam inlet and a delayed fluorescence outlet;
    a fused silica lens system for delivering said excitation beam to said sample in said sample enclosure;
    sample handling means capable of positioning the so-reacted sample in the path of said excitation beam within said sample enclosure;
    means for measuring delayed fluorescence emitted from the so-reacted sample;
    a fused silica lens system for delivering the delayed flurescence emitted from the sample to said delayed fluorescence measuring means; and
    controller means to control the sequence and coordination of said fluorometer.

2. The time-resolved fluorometer of claim 1 wherein said means for emitting a beam of excitation light comprises a pulsed dye laser.

3. The time-resolved fluorometer of claim 2 which further comprises means for monitoring laser pulse output level.

4. The time-resolved fluorometer of claim 2 wherein said controller comprises a pulse-producing clock which controls laser pulse rate and delay timings.

5. The time-resolved fluorometer of claim 1 wherein said fused silica lens system for excitation beam delivery comprises an interference filter of metal on a fused silica base.

6. The time-resolved fluorometer of claim 5 wherein the interference filter passes 405 nm incident light and reflects incident light having a wavelength of at least 565 nm.

7. The time-resolved fluorometer of claim 1 wherein the sample excitation station has therein a front reflecting surface parabolic mirror having an opening in the center thereof, which mirror is perpendicular to and centered on the excitation beam axis such that excitation beam light passes through the center thereof and emission light is reflected to the emission beam outlet.

8. The time-resolved fluorometer of claim 1 wherein said measuring means comprises a photomultiplier operating in a photon-couting mode.

9. The time-resolved fluorometer of claim 1 wherein said fused silica lens system for delayed fluorescence emission comprises a fused silica convergent lens.

10. The time-resolved fluorometer of claim 1 wherein said fused silica lens system for delayed fluorescence emission further comprises a fused silica interference filter.

11. The time-resolved fluorometer of claim 2 wherein said fused silica lens system for delayed fluorescence emission comprises a fused silica convergent lens associated with the outlet of said sample excitation station and an interference filter formed on a fused silica substrate and associated with said means for measuring delayed fluorescence.

12. The time-resolved fluorometer of claim 9 wherein the means for measuring delayed fluorescence comprises a photomultiplier that receives emission beam pulses from the delayed fluorescence outlet, a preamplifier that receives and amplifies electric pulses from the photomultiplier, a discriminator that receives pulses from the preamplifier and selectively passes only pulses of at least a predetermined voltage and an event counter that receives and counts pulses from the discriminator, and wherein the coordination of and reporting by the means for measuring delayed fluorescence is controlled by the controller of the time-resolved fluorometer.

13. The time-resolved fluorometer of claim 2 wherein said time-resolved fluorometer comprises a thermoelectrically cooled photomultiplier.

14. The time-resolved fluorometer of claim 13 wherein said photomultiplier is cooled to −40° C. during operation.

15. The time-resolved fluorometer of claim 13 which further comprises a thermostat and temperature controller.

16. The time-resolved fluorometer of claim 13 which further comprises means for monitoring laser pulse output level.

17. The time-resolved fluorometer of claim 11 wherein said controller comprises a pulse-producing clock which controls laser pulse rate and delay timing.

18. The time-resolved fluorometer of claim 11 wherein said fused silica lens system for excitation beam delivery comprises an interference filter of metal on a fused silica base.

19. The time-resolved fluorometer of claim 18 wherein the interference filter passes 405 nm incident light and reflects incident light having a wavelength of at least 565 nm.

20. The time-resolved fluorometer of claim 1 wherein said fused silica delayed fluorescence delivery lens system comprises a first and a second filter wherein said first filter prevents scattered incident radiation or direct fluorescence from reaching said second filter.

21. The time-resolved fluorometer of claim 11 wherein said measuring means comprises a photomultiplier operating in a photon-counting mode.

22. The time-resolved fluorometer of claim 13 wherein said controller comprises a pulse-producing clock which controls laser pulse rate and delay timings.

23. The time-resolved fluorometer of claim 13 wherein said fused silica lens system for excitation beam delivery comprises an interference filter of metal on a fused silica base.

24. The time-resolved fluorometer of claim 23 wherein the interference filter passes incident light of about 405 nm and reflects incident light having a wavelength of at least about 565 nm.

25. The time-resolved fluorometer of claim 13 wherein said measuring means comprises a photomultiplier operating in a photon-counting mode.

26. The time-resolved fluorometer of claim 13 wherein said fused silica lens system for delayed fluorescence emission further comprises a fused silica interference filter.

27. The time-resolved fluorometer of claim 26 wherein the means for measuring delayed fluorescence comprises a photomultiplier that receives emission beam pulses from the delayed fluorescence outlet, a preamplifier that receives and amplifies electric pulses from the photomultiplier, a discriminator that receives pulses from the preamplifier and selectively passes only pulses of at least a predetermined voltage and an event counter that receives and counts pulses from the discriminator, and wherein the coordination of and reporting by the means for measuring delayed fluorescence is controlled by the controller of the time-resolved fluorometer.

* * * * *